(12) United States Patent
Joo et al.

(10) Patent No.: US 8,222,329 B2
(45) Date of Patent: Jul. 17, 2012

(54) SYMMETRIC CYCLIC PHOSPHONATE COMPOUND, METHOD OF PREPARING THE SAME AND FLAME RETARDANT STYRENIC RESIN COMPOSITION INCLUDING THE SAME

(75) Inventors: Beom Jun Joo, Seoul (KR); Sang Hyen Hong, Seoul (KR); Min Soo Lee, Seoul (KR); Byun Kun Lee, Gunpo-si (KR)

(73) Assignee: Cheil Industries Inc., Gumi-si (KR)

( * ) Notice: Subject to any disclaimer, the term of this patent is extended or adjusted under 35 U.S.C. 154(b) by 0 days.

(21) Appl. No.: 12/700,904

(22) Filed: Feb. 5, 2010

(65) Prior Publication Data
US 2010/0137482 A1    Jun. 3, 2010

Related U.S. Application Data

(62) Division of application No. 12/335,611, filed on Dec. 16, 2008, now abandoned.

(30) Foreign Application Priority Data

Dec. 20, 2007 (KR) .............................. 2007-0134123
Oct. 8, 2008 (KR) .............................. 2008-0098437

(51) Int. Cl.
*C07F 9/547* (2006.01)
*C07F 9/576* (2006.01)
*C07F 9/02* (2006.01)
*C07F 9/6571* (2006.01)
*C08K 5/49* (2006.01)
*C08K 5/51* (2006.01)

(52) U.S. Cl. ........ 524/119; 524/115; 524/116; 524/117; 524/127; 524/132; 524/133; 558/83; 558/77; 252/601; 252/609

(58) Field of Classification Search .................. 524/119, 524/115, 116, 117, 127, 132, 133; 252/601, 252/609; 558/83, 77
See application file for complete search history.

(56) References Cited

U.S. PATENT DOCUMENTS

| | | | | |
|---|---|---|---|---|
| 4,402,882 A | * | 9/1983 | Kiefer | 558/77 |
| 4,520,152 A | * | 5/1985 | Axelrod | 524/120 |
| 2008/0125526 A1 | * | 5/2008 | Bae et al. | 524/127 |
| 2009/0163627 A1 | | 6/2009 | Joo et al. | |

FOREIGN PATENT DOCUMENTS

| | | | |
|---|---|---|---|
| FR | 1503429 | * | 10/1967 |
| FR | 1503429 A | | 11/1967 |
| JP | 2002-037973 A | | 2/2002 |

* cited by examiner

*Primary Examiner* — James J Seidleck
*Assistant Examiner* — Deve E Valdez
(74) *Attorney, Agent, or Firm* — Summa, Additon & Ashe, P.A.

(57) ABSTRACT

Disclosed herein is a symmetric cyclic phosphonate compound represented by the following Formula 1, a method of preparing the same and a flame retardant styrenic resin composition including the same:

[Formula 1]

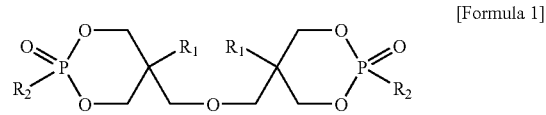

wherein $R_1$ and $R_2$ are each independently hydrogen, $C_1$-$C_6$ alkyl or $C_6$-$C_{20}$ aryl. The styrene resin composition employing the symmetric cyclic phosphonate compound exhibits good flame retardancy and impact strength, does not release halide gas during preparation or combustion of the resin composition, and thus is environmentally friendly.

14 Claims, 6 Drawing Sheets

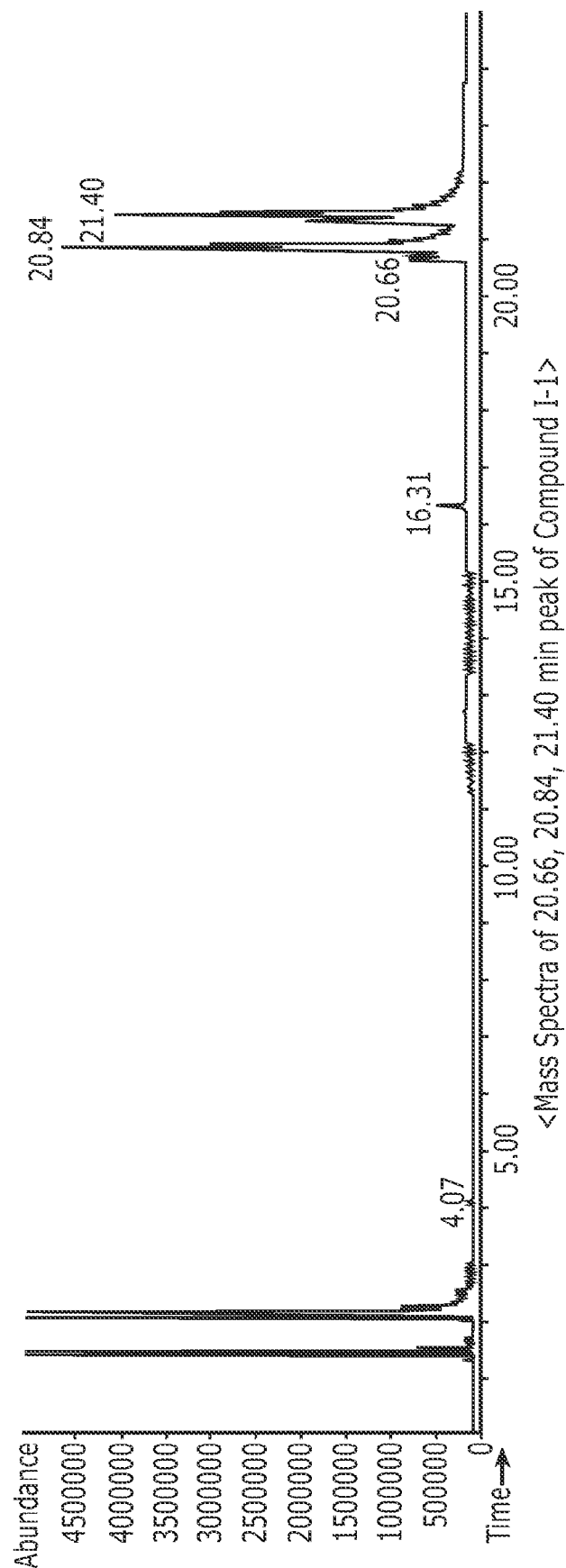

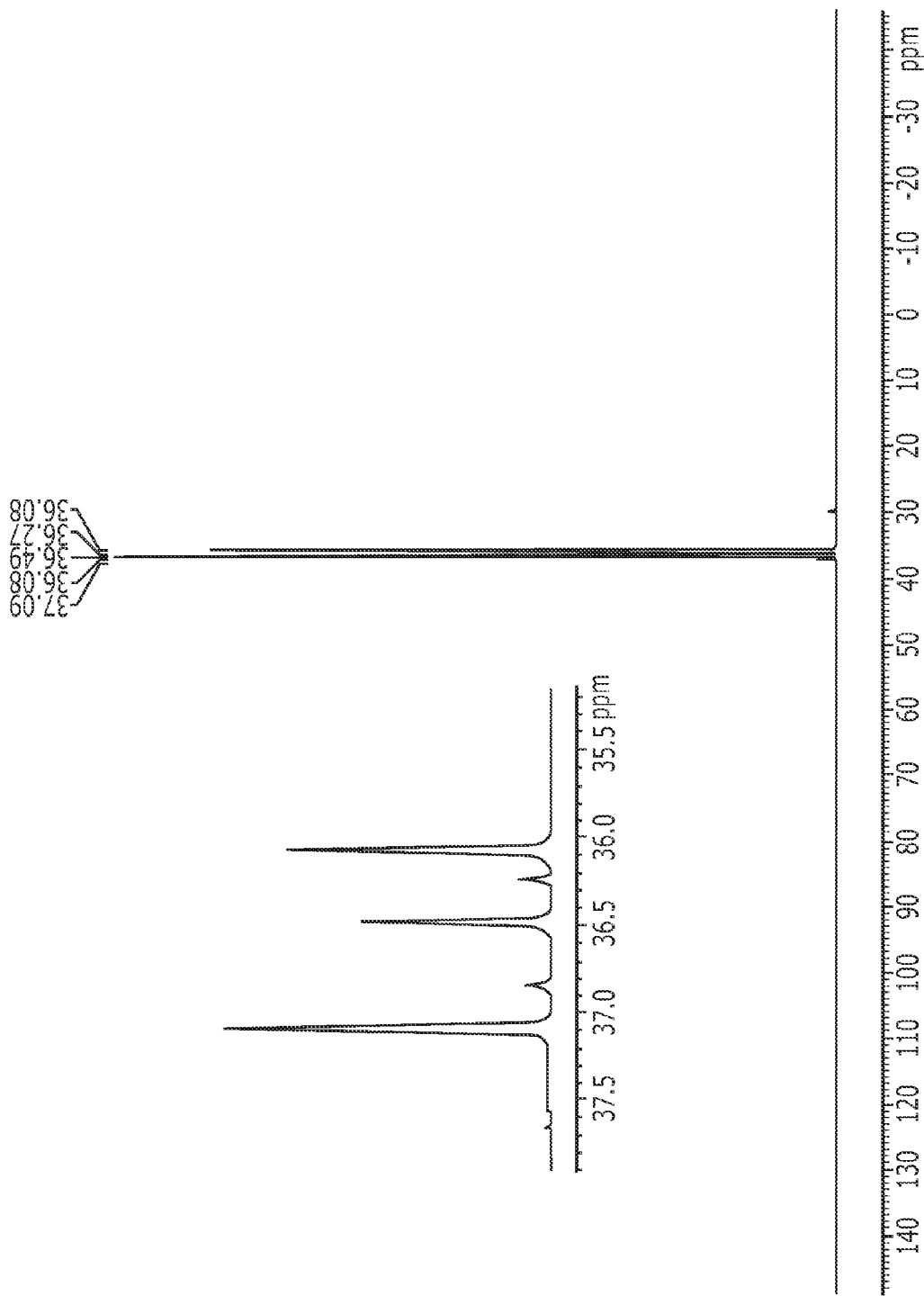

SYMMETRIC CYCLIC PHOSPHONATE COMPOUND, METHOD OF PREPARING THE SAME AND FLAME RETARDANT STYRENIC RESIN COMPOSITION INCLUDING THE SAME

CROSS-REFERENCE TO RELATED APPLICATIONS

This application is a divisional application of U.S. Ser. No. 12/335,611, filed Dec. 16, 2008, which application claims priority from Korean Patent Application No. 10-2007-0134123, filed Dec. 20, 2007, in the Korean Intellectual Property Office, and Korean Patent Application No. 10-2008-0098437, filed Oct. 8, 2008, in the Korean Intellectual Property Office, wherein the disclosure of each of the foregoing applications is incorporated herein by reference in its entirety.

FIELD OF THE INVENTION

The present invention relates to a novel phosphonate compound and a flame retardant styrenic resin composition including the same.

BACKGROUND OF THE INVENTION

Generally, styrenic resins have good processability and mechanical properties and have accordingly been used to produce housing parts for many electrical and electronic goods. However, because styrenic resins can be readily ignited, they are not able to resist fire. Particularly, once styrenic resins catch on fire by external ignition sources, they can further spread fire. Moreover, styrenic resins are subject to various mandatory controls on flammability for safety reasons in countries such as the United States, Japan and Europe, and are required to have high flame retardancy to meet the Underwriter's Laboratories Standard for use in the housings of electrical and electronic appliances. Accordingly, there is a need render styrenic resins flameproof to broaden their use in different applications.

A widely used and known method for imparting good flame retardancy to styrenic resin comprises adding a halogen-containing compound as a flame retardant to a rubber-modified styrenic resin and adding an antimony-containing compound as a flame retardant aid. Examples of halogen-containing compounds used to impart flame retardancy include polybromodiphenyl ether, tetrabromobisphenol-A, epoxy compounds substituted with bromine, chlorinated polyethylene, and the like. Antimony trioxide or antimony pentaoxide is commonly used as an antimony-containing compound.

When a halogen- and antimony-containing compound is used to improve flame retardancy of resins, a desired degree of flame retardancy can readily be imparted to the resulting products without significantly degrading the physical properties thereof. Therefore, the halogen- and antimony-containing compounds are widely used as the primary flame retardant for housing materials of electrical appliances and office equipment formed of ABS resins, PS resins, PBT resins, PET resins or epoxy resins. However, hydrogen halide gases released by halogen-containing compounds during processing can have fatal effects on the human body and have high environmental persistence because these compounds are not naturally degradable. Also these compounds are not soluble in water, and thus can be highly bioaccumulated. Particularly, polybromodiphenyl ether, which is widely used as a halogen-containing flame retardant, may produce toxic gases such as dioxin or furan during combustion, and is consequently harmful to humans and the environment. Accordingly, there is a need to develop flame retardancy methods that do not employ halogen-containing compounds.

SUMMARY OF THE INVENTION

Accordingly, the present invention is directed to a novel symmetric cyclic phosphonate compound and a highly flame retardant styrenic resin composition including the symmetric cyclic phosphonate compound.

Aspects of the present invention provide a novel symmetric cyclic phosphonate compound that can exhibit excellent flame retardancy and a method of preparing the same.

Aspects of the present invention also provide a flame retardant resin composition which includes the symmetric cyclic phosphonate compound as a flame retardant and which is environmentally friendly.

Aspects of the present invention also provide a flame retardant resin composition which can be prepared by adding the symmetric cyclic phosphonate compound as a flame retardant and decreasing the amount of polyphenylene ether added to the composition. The composition of the invention thus can exhibit good impact resistance and mold processability.

These and other objects of the present invention will be accomplished by the present invention as described below.

According to an aspect of the present invention, there is provided a novel symmetric cyclic phosphonate compound represented by the following Formula 1:

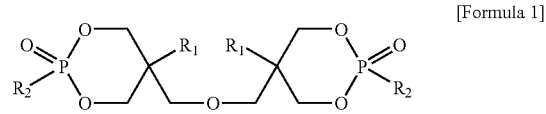

[Formula 1]

wherein $R_1$ and $R_2$ are each independently hydrogen, $C_1$-$C_6$ alkyl or $C_6$-$C_{20}$ aryl.

In exemplary embodiments of the present invention, the phosphate compound represented by Formula 1 may be prepared by reacting a phosphonic dichloride represented by the following Formula 2 with a polyol represented by the following Formula 3 in the presence of a base:

[Formula 2]

wherein $R_2$ is hydrogen, $C_1$-$C_6$ alkyl or $C_6$-$C_{20}$ aryl;

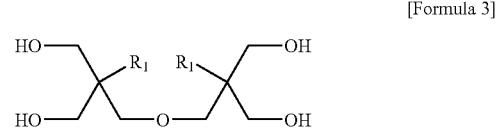

[Formula 3]

wherein $R_1$ is hydrogen, $C_1$-$C_6$ alkyl or $C_6$-$C_{20}$ aryl.

According to exemplary embodiments of the present invention, a flame retardant styrenic resin composition may include about 100 parts by weight of a base resin comprising (A) a styrenic resin and (B) a polyphenylene ether resin; and about 0.5 to about 50 parts by weight of (C) the symmetric cyclic phosphonate compound represented by Formula 1.

In one exemplary embodiment of the present invention, the base resin may include about 60 to about 99% by weight of the styrenic resin (A) and about 1 to about 40% by weight of the polyphenylene ether resin (B).

In another exemplary embodiment of the present invention, the resin composition may further include about 0.1 to about 40 parts by weight of (D) an aromatic phosphate ester compound, (E) a phosphate compound or a mixture thereof, based on about 100 parts by weight of the base resin (A)+(B).

BRIEF DESCRIPTION OF THE DRAWINGS

FIG. 3 illustrates a PNMR analysis result of a symmetric cyclic phosphonate compound (I-1) prepared in Example 1 of the present invention.

DETAILED DESCRIPTION OF THE INVENTION

Figure 1B:
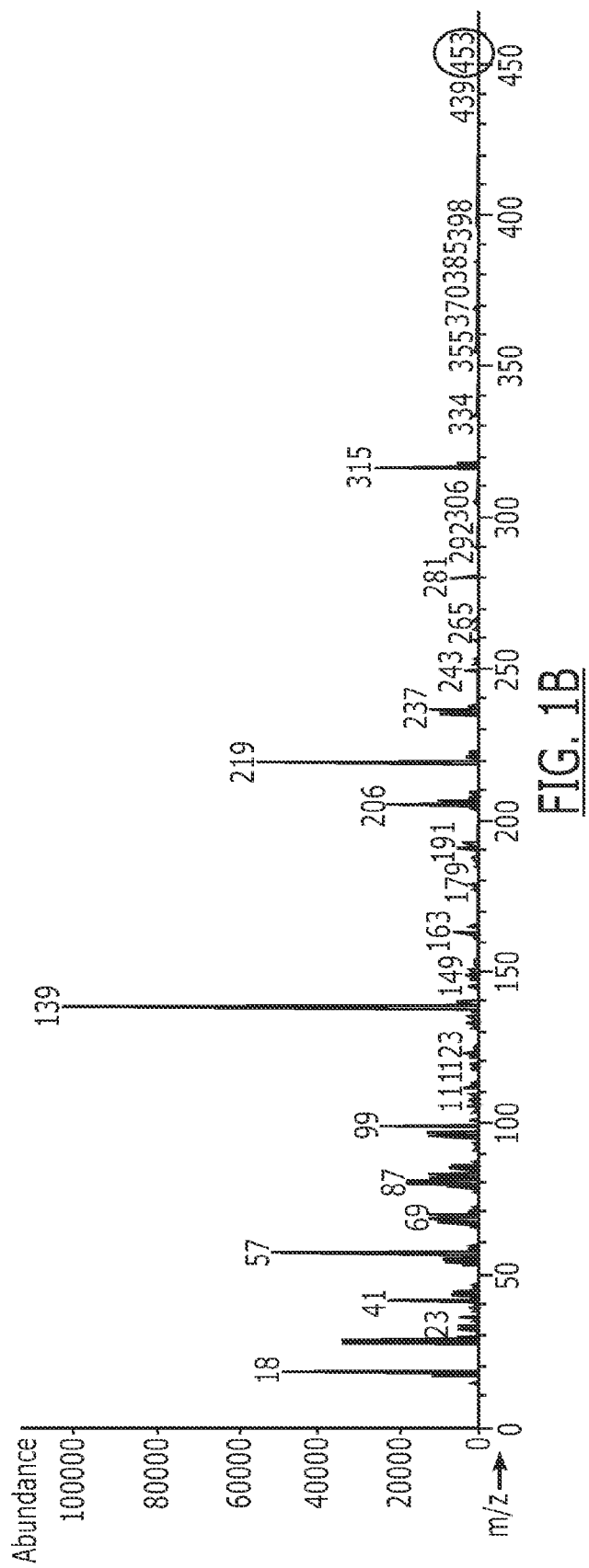
FIG. 1 illustrates a GC-MS analysis result of a symmetric cyclic phosphonate compound (I-1) prepared in Example 1 of the present invention.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

Symmetric Cyclic Phosphonate Compound

A symmetric cyclic phosphonate compound according to the present invention can be represented by the following Formula 1:

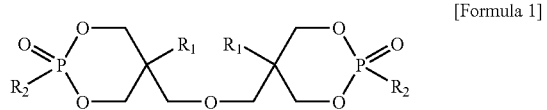

[Formula 1]

wherein $R_1$ and $R_2$ are each independently hydrogen, $C_1$-$C_6$ alkyl or $C_6$-$C_{20}$ aryl.

$R_1$ and $R_2$ can each be independently $C_1$-$C_6$ alkyl. For example, $R_1$ and $R_2$ can each be independently methyl, ethyl, propyl, isopropyl, n-butyl, sec-butyl, isobutyl, tert-butyl or isoamyl.

An exemplary phosphonate compound represented by the Formula 1 may include a compound represented by the following Formula I-1:

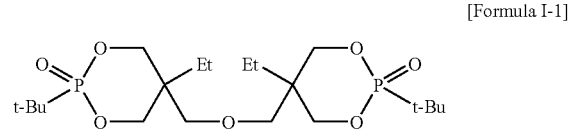

[Formula I-1]

wherein Et is ethyl and t-Bu is tert-butyl.

Method of Preparing the Symmetric Cyclic Phosphonate Compound

The present invention provides a method of synthesizing the symmetric cyclic phosphonate compound.

The symmetric cyclic phosphonate compound can be prepared by reacting a phosphonic dichloride represented by the following Formula 2 with a polyol represented by the following Formula 3 in the presence of a base:

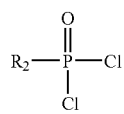

[Formula 2]

wherein $R_2$ is hydrogen, $C_1$-$C_6$ alkyl or $C_6$-$C_{20}$ aryl;

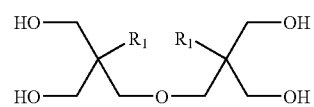

[Formula 3]

wherein $R_1$ is hydrogen, $C_1$-$C_6$ alkyl or $C_6$-$C_{20}$ aryl.

In exemplary embodiments of the present invention, the phosphonic dichloride represented by Formula 2 may be reacted under reflux with the polyol represented by Formula 3.

For example, about 2 equivalents of the phosphonic dichloride represented by Formula 2 may be reacted with about 1 equivalent of the polyol represented by Formula 3 in the presence of a base and a solvent. The reaction temperature may be from about 80 to about 200° C., for example from about 100 to about 150° C. The reaction may be conducted for from about 5 to about 20 hours, for example from about 7 to about 15 hours.

The base can be used in an amount of greater than or equal to about 4 equivalents per about 1 equivalent of the polyol represented by Formula 3. The base used in the present invention is not particularly limited. For example, the base can include triethylamine, pyridine, sodium hydroxide and the like, and combinations thereof. The solvent used in the present invention has no particular restriction and can be any conventional organic solvent, for example, toluene, benzene, xlyene, 1,4-dioxane, methyl chloride and the like, and combinations thereof.

The symmetric cyclic phosphonate compound of the present invention has a symmetric structure, and thus is high in phosphorus content. Therefore, when the symmetric cyclic phosphonate compound is used as a flame retardant, it can exhibit good flame retardancy. Additionally, the symmetric cyclic phosphonate compound does not release halide gases during processing or combustion, and accordingly, is environmentally friendly.

Flame Retardant Styrenic Resin Composition

The present invention provides a flame retardant resin composition employing the symmetric cyclic phosphonate compound as a flame retardant.

In one exemplary embodiment of the present invention, a non-halogen flame retardant styrenic resin composition which employs the symmetric cyclic phosphonate compound to a styrenic resin is provided.

The non-halogen flame retardant styrenic resin composition comprises about 100 parts by weight of a base resin comprising (A) a styrenic resin and (B) a polyphenylene ether resin; and about 0.5 to about 50 parts by weight of (C) the symmetric cyclic phosphonate compound represented by Formula 1 or a combination thereof. Details of each of components will be described below.

(A) Styrenic Resin

The styrenic resin (A) that can be used in the resin composition of the president invention may include, without limitation, a polystyrene resin, a rubber modified aromatic vinyl resin (such as a rubber modified aromatic vinyl-cyanide vinyl graft copolymer resin), a rubber modified high impact polystyrene resin (HIPS), and the like, and combinations thereof.

The styrenic resin (A) can be generally polymerized in the presence of an initiator, but can be polymerized with heat and no initiator. The initiator may include, without limitation, one or more selected from the group consisting of organic peroxides such as benzoyl peroxide, t-butyl hydroperoxide, acetyl peroxide and cumene hydroperoxide, azo compounds such as azobisisobutyronitrile, and the like, and combinations thereof.

Polymerization methods for making the styrenic resin (A) can include bulk polymerization, suspension polymerization, emulsion polymerization or a combination thereof.

The rubber used in the polymerization of the styrenic resin (A) can include, without limitation, polybutadiene, polyisoprene, styrene-butadiene copolymer, alkyl acrylic rubber, ethylene-propylene-diene terpolymer (EPDM), ethylene/propylene rubber, silicon rubber and the like, and combinations thereof. The amount of the rubber used can be about 3 to about 30% by weight, for example about 5 to about 15% by weight, based on a total weight of the styrenic resin.

Monomers used in the polymerization of the styrenic resin (A) can include aromatic mono-alkenyl monomers, such as but not limited to styrene, α-methyl styrene, and the like, and combinations thereof, and can be used in an amount of about 70 to about 90% by weight, for example about 85 to about 90% by weight, based on a total weight of the styrenic resin.

The styrenic resin (A) can be prepared by optionally adding one or more additional monomers copolymerizable with the aromatic mono-alkenyl monomer, such as an alkyl ester monomer, an unsaturated nitrile monomer such as acrylonitrile, methacrylonitrile, and the like, or a combination thereof. Other monomers copolymerizable with the aromatic mono-alkenyl monomer, such as acrylic acid, methacrylic acid, maleic anhydride, N-substituted maleimide and the like, or a combination thereof can also be added to the monomers and polymerized to impart properties such as chemical resistance, processability and heat resistance to the polymer. These can be added in an amount of about 0 to about 40 parts by weight per 100 parts by weight of a total weight of the monomers.

The average size of rubber particles can range from about 0.1 to about 4.0 μm to optimize physical properties when blending a styrenic resin and polyphenylene ether.

The styrenic resin (A) can be used in an amount of about 60 to about 99% by weight, for example about 65 to about 90% by weight, and as another example about 70 to about 85% by weight, based on a total weight of the base resin (A)+(B).

(B) Polyphenylene Ether Resin

The resin composition according to the present invention may employ a polyphenylene ether resin (B) with the styrenic resin (A) as a base resin to further improve flame retardancy and heat resistance.

Examples of the polyphenylene ether resin (B) can include, without limitation, poly(2,6-dimethyl-1,4-phenylene) ether, poly(2,6-diethyl-1,4-phenylene) ether, poly(2,6-dipropyl-1,4-phenylene) ether, poly(2-methyl-6-ethyl-1,4-phenylene) ether, poly(2-methyl-6-propyl-1,4-phenylene) ether, poly(2-ethyl-6-propyl-1,4-phenylene) ether, poly(2,6-diphenyl-1,4-phenylene) ether, copolymer of poly(2,6-dimethyl-1,4-phenylene) ether and poly(2,3,6-trimethyl-1,4-phenylene) ether, copolymer of poly(2,6-dimethyl-1,4-pheylene) ether and poly(2,3,5-triethyl-1,4-phenylene) ether, and the like. These can be used alone or as a combination thereof.

The degree of polymerization of the polyphenylene ether resin (B) is not limited specifically, but can vary depending on factors such as heat-stability or processability of the resin composition. The intrinsic viscosity of the polyphenylene ether resin may be in the range of about 0.2 to about 0.8 measured in chloroform solvent at 25° C.

The polyphenylene ether resin (B) of the present invention can be used in an amount of about 1 to about 40% by weight, for example about 10 to about 35% by weight, and as another example about 15 to about 30% by weight, based on a total weight of the base resin (A)+(B).

When the polyphenylene ether is used in an amount of greater than about 40% by weight, processability can be deteriorated. In addition when the polyphenylene ether is used in an amount of less than about 1% by weight, flame retardancy may tend to decrease significantly.

(C) Symmetric Cyclic Phosphonate Compound

The symmetric cyclic phosphonate compound used in the resin composition of the present invention can be a compound represented by the following Formula 1 or a combination thereof:

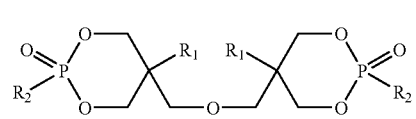

[Formula 1]

wherein $R_1$ and $R_2$ are each independently hydrogen, $C_1$-$C_6$ alkyl or $C_6$-$C_{20}$ aryl.

The symmetric cyclic phosphonate compound (C) represented by Formula 1 can be used in an amount of about 0.5 to about 50 parts by weight, for example about 1 to about 40 parts by weight, and as another example about 2.5 to about 35 parts by weight, based on about 100 parts by weight of the base resin (A)+(B).

When the symmetric cyclic phosphonate compound (C) is used in an amount of greater than about 50 parts by weight, physical properties such as mechanical strength can be deteriorated. When the symmetric cyclic phosphonate compound (C) is used in an amount of less than about 0.5 parts by weight, flame retardancy tends to decrease.

In one exemplary embodiment of the present invention, the resin composition may further comprise (D) an aromatic phosphate ester compound, (E) a phosphate compound or a mixture thereof in order to further improve flame retardancy.

The aromatic phosphate ester compound (D), the phosphate compound (E) or a combination thereof can be used in an amount of about 0.1 to about 40 parts by weight, for example about 5 to about 30 parts by weight, and as another example about 10 to about 25 parts by weight, based on about 100 parts by weight of the base resin (A)+(B). When the aromatic phosphate ester compound (D), the phosphate compound (E) or the mixture thereof are used in an amount of less than about 0.1 parts by weight, it may be difficult to achieve improved flame retardant effect. In addition, when the aromatic phosphate ester compound (D), the phosphate compound (E) or the mixture thereof are used in an amount of greater than about 40 parts by weight, physical properties such as mechanical strength may be deteriorated.

When the aromatic phosphate ester compound (D) and the phosphate compound (E) are used together, the aromatic phosphate ester compound (D) can be used in an amount of about 0.05 to about 30 parts by weight, and the phosphate compound (E) can be used in an amount of about 0.05 to about 10 parts by weight, based on about 100 parts by weight of the base resin (A)+(B).

Details of the aromatic phosphate ester compound (D) and the phosphate compound (E) will be described below.

(D) Aromatic Phosphate Ester Compound

The aromatic phosphate ester compound used in the present invention can have a structure represented by the following Formula 4:

[Formula 4]

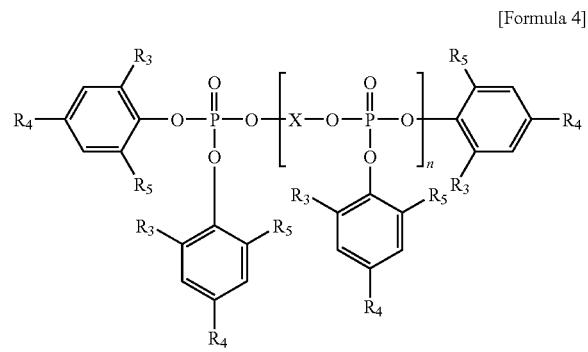

wherein $R_3$, $R_4$ and $R_5$ are each independently hydrogen or $C_1$-C4 alkyl; X is $C_6$-$C_{20}$ aryl or alkyl-substituted $C_6$-$C_{20}$ aryl that is a derivative from, for example, resorcinol, hydroquinol or bisphenol-A; and n is an integer of 0 to 4.

Where n is 0, examples of the compound represented by Formula 4 can include, without limitation, triphenyl phosphate, tri(2,6-dimethyl) phosphate, and the like, and where n is 1, examples of the compound can include, without limitation, resorcinol bis(diphenyl) phosphate, resorcinol bis(2,6-dimethyl phenyl) phosphate, resorcinol bis(2,4-ditertiary butyl phenyl) phosphate, hydroquinol bis(2,6-dimethyl phenyl) phosphate, hydroquinol bis(2,4-ditertiary butyl phenyl) phosphate, and the like. The aromatic phosphate ester compound (D) can be used alone or in combination thereof.

(E) Phosphate Compound

The phosphate compound used in the present invention can be an alkyl phosphinic acid metal salt and have a structure represented by the following Formula 5:

[Formula 5]

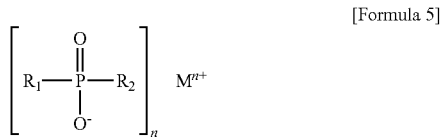

wherein $R_1$ and $R_2$ are each independently hydrogen or $C_1$-$C_4$ alkyl; M is a metal selected from the group consisting of Al, Mg, K, Zn and Ca; and n is an integer of 1 to 3.

Examples of the alkyl phosphinic acid metal salt can include without limitation diethyl phosphinic acid aluminum salt.

In another exemplary embodiment of the present invention, in addition to the above-described components, the resin composition can further comprise various additives. Examples of the additive can include without limitation a heat stabilizer, an anti-drip agent, an anti-oxidant, a compatibilizer, a light stabilizer, a plasticizer, a pigment, a dye, an inorganic filler and the like. Examples of the inorganic filler can include without limitation glass fiber, asbestos, talc, ceramic, sulfonate and the like. The additive can be used alone or in combination thereof. The additive can be used in an amount of less that or equal to about 30 parts by weight, for example in an amount of about 0.001 to about 30 parts by weight, based on about 100 parts by weight of the base resin (A)+(B).

The resin composition of the present invention can be prepared by conventional methods employed in the manufacture of resin compositions. For example, the above-described components and additives can be mixed together, and the mixture melted and extruded with an extruder into pellets.

The resin composition according to the present invention has good flame retardancy and impact strength, and thus can be used for many products. The resin composition can be widely used for the manufacture of electrical devices and electronic devices such as TVs, computers, audio systems, air conditioners, office automations and the like, which are subject to strict Underwriters' Laboratories Standard for flame retardancy.

The present invention may be better understood by reference to the following examples. The following examples are intended for the purpose of illustration and are not be construed as in any way limiting the scope of the present invention, which is defined in the claims appended hereto.

EXAMPLES

Example 1

Preparation of the Symmetric Cyclic Phosphonate Compound 2 equivalents of t-butyl phosphonic dichloride (IV) is reacted under reflux with 1 equivalent of tetraol (V) and 4 equivalents of triethylamine in the presence of toluene solvent at a temperature of 130° C. for 10 hours. After completion of the reaction, water is added, and the reaction mixture is stirred until solids disappeared. Then, the organic layer is separated and distilled in vacuum to obtain a symmetric cyclic phosphonate compound (I-1) having a purity of 99% and with a yield of 50%.

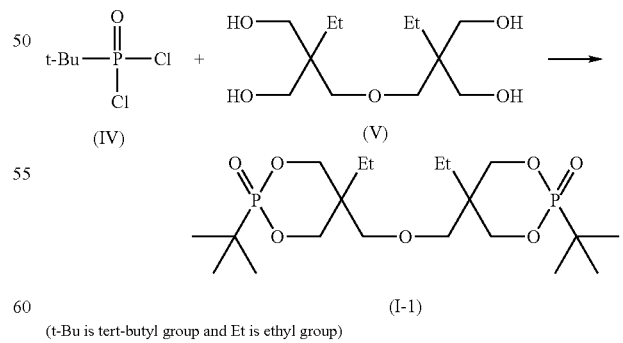

(t-Bu is tert-butyl group and Et is ethyl group)

Figure 1C:
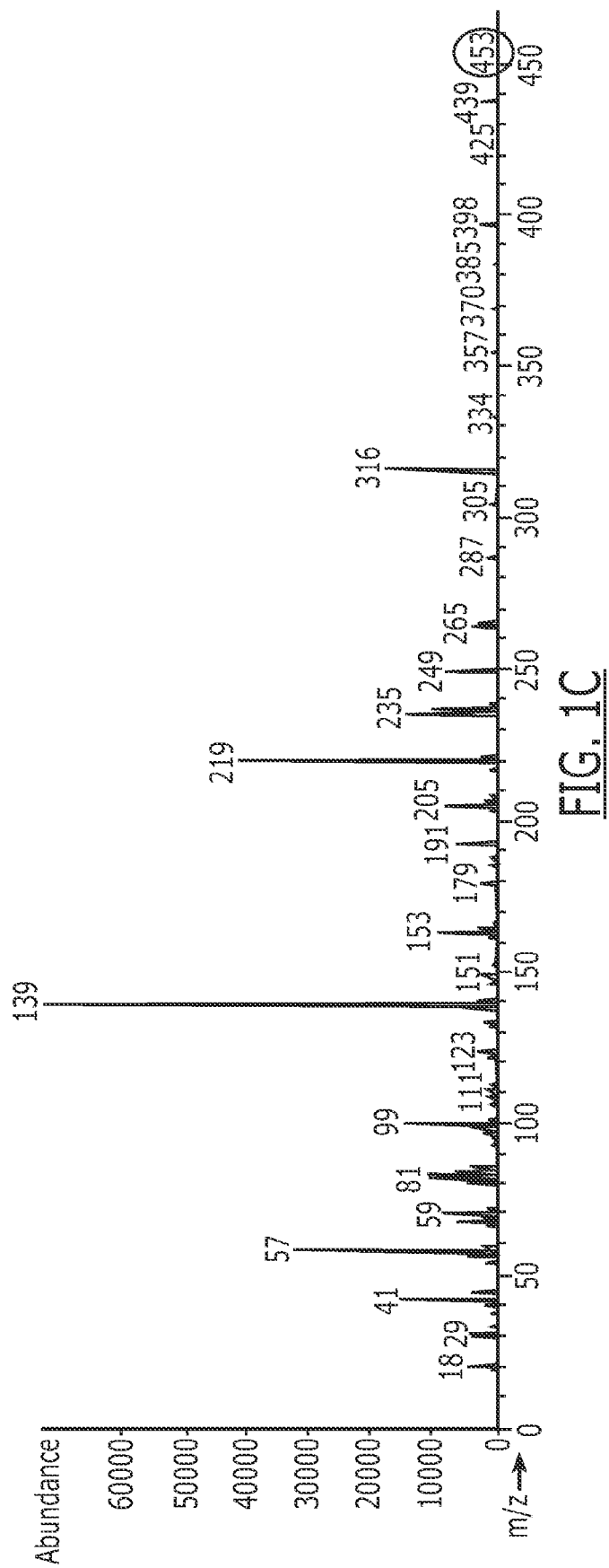
Figure 1D:
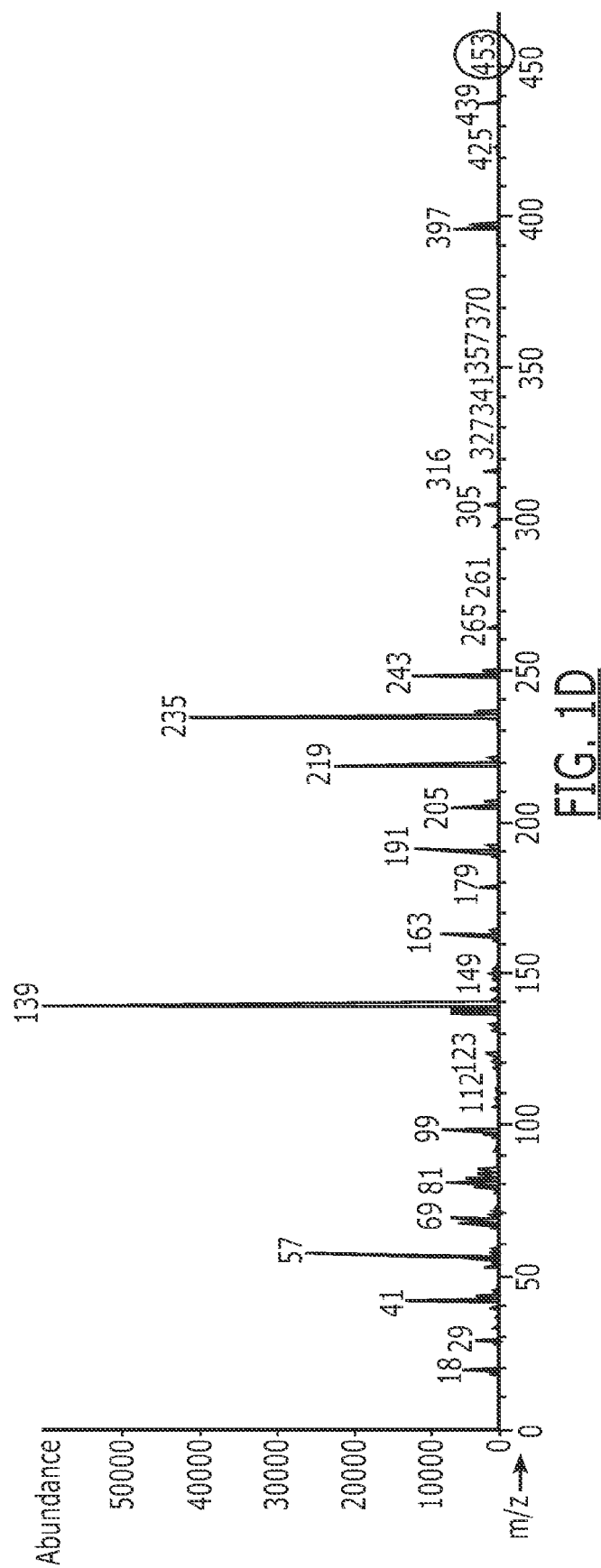
Figure 2:
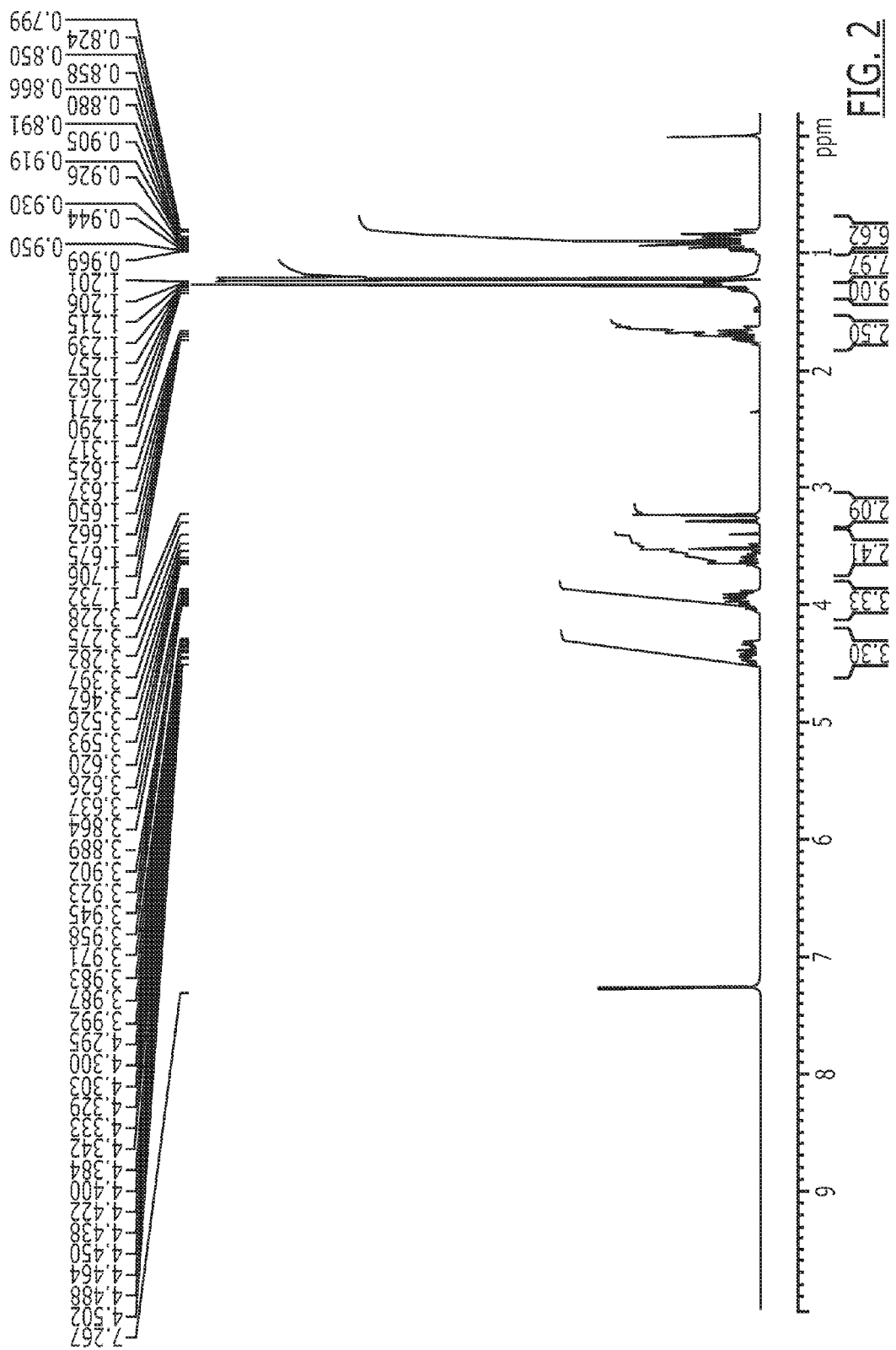
FIG. 2 illustrates a $^1$H-NMR analysis result of a symmetric cyclic phosphonate compound (I-1) prepared in Example 1 of the present invention.

GC-MS analysis, $^1$H-NMR analysis and PNMR analysis are conducted on the resulting symmetric cyclic phosphonate compound (I-1). The results are shown in FIGS. 1 to 3, respectively.

Preparation of the Flame Retardant Resin Composition

The following components are used to prepare a flame-proof resin composition in the following examples and comparative examples.

(A) Styrenic Resin

A rubber modified styrenic resin manufactured by Cheil Industries Inc. (product name: HG-1760S) is used.

(B) Polyphenylene Ether Resin (PPE)

A poly(2,6-dimethyl-phenylene) ether manufactured by Mitsubishi Engineering-Plastics Corp. of Japan (product name: PX-100F) is used. The polyphenylene ether resin is in powder form having an average particle size of several dozen micrometers (μm).

(C) Symmetric Cyclic Phosphonate Compound

The symmetric cyclic phosphonate compound prepared in Example 1 is used.

(D) Aromatic Phosphate Ester Compound

A bisphenol-A bis(diphenyl) phosphate manufactured by Daihachi Chemical Industry Co., Ltd. of Japan (product name: CR741S) is used.

(E) Phosphate Compound

A diethyl phosphinic acid aluminum salt manufactured by Clariant Co. (product name: Exolit OP930) is used.

Examples 2-7

Components as shown in below Table 1 are mixed, and the mixture is extruded at a temperature of 200 to 280° C. with a conventional twin-screw extruder into pellets. The pellets are then dried at 80° C. for 2 hours, and molded into test specimens using a 6-oz injection molding machine at a temperature of 180 to 280° C. and mold temperature of 40 to 80° C. The flame retardancy is measured in accordance with UL94VB using test specimens having a thickness of ⅛". The impact strength is measured in accordance with ASTM D256 (⅛", kg·cm/cm) using test specimens having a thickness of ⅛". The test results are shown in Table 1 below.

Comparative Examples 1-2

Comparative Examples 1-2 are prepared in the same manner as in Examples 2-7 except that each of the components is used as shown in below Table 1. The test results are shown in Table 1 below.

TABLE 1

| | Examples | | | | | | Comparative Examples | |
|---|---|---|---|---|---|---|---|---|
| | 2 | 3 | 4 | 5 | 6 | 7 | 1 | 2 |
| A | 85 | 85 | 85 | 75 | 75 | 70 | 85 | 85 |
| B | 15 | 15 | 15 | 25 | 25 | 30 | 15 | 15 |
| C | 20 | 2.5 | 35 | 20 | 2.5 | 20 | — | — |
| D | — | 15 | — | — | 15 | — | 15 | 20 |
| E | — | 2.5 | — | — | 2.5 | — | 5 | — |
| UL94 Flame Retardancy (⅛") | V-1 | V-1 | V-0 | V-0 | V-0 | V-0 | V-1 | Fail |
| IZOD Impact Strength (⅛", kg·cm/cm) | 7.64 | 4.06 | 8.12 | 8.05 | 6.52 | 8.21 | 3.08 | 4.88 |

As shown in Table 1, it can be seen that Examples 2-7 including the symmetric cyclic phosphonate compound of the present invention as a flame retardant exhibit good flame retardancy and impact strength under a thickness of ⅛", compared with Comparative Example 1 including both the aromatic phosphate ester compound and the phosphate compound, and Comparative Example 2 including the aromatic phosphate ester compound alone.

In addition, it can also be seen that since the symmetric cyclic phosphonate compound of the present invention has a symmetric structure, the symmetric cyclic phosphonate compound is high in phosphorous content and exhibits excellent flame retardancy. Moreover, the symmetric cyclic phosphonate compound does not contain halogen. Therefore, the symmetric cyclic phosphonate compound does not release hydrogen halide gases during processing or combustion, and accordingly is environmentally friendly.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A flame retardant styrenic resin composition comprising:

about 100 parts by weight of a base resin comprising (A) a styrenic resin and (B) a polyphenylene ether resin; and about 0.5 to about 50 parts by weight of (C) a symmetric cyclic phosphonate compound represented by the following Formula 1 or a combination thereof;

[Formula 1]

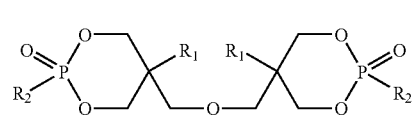

wherein $R_1$ and $R_2$ are each independently hydrogen or $C_1$-$C_6$ alkyl.

2. The flame retardant styrenic resin composition of claim 1, wherein said base resin comprises about 60 to about 99% by weight of said styrenic resin (A) and about 1 to about 40% by weight of said polyphenylene ether resin (B), based on the total weight of the base resin comprising (A)+(B).

3. The flame retardant styrenic resin composition of claim 1, further comprising about 0.1 to about 40 parts by weight of (D) an aromatic phosphate ester compound, (E) a phosphate compound or a combination thereof, based on about 100 parts by weight of said base resin (A)+(B).

4. The flame retardant styrenic resin composition of claim 3, wherein said aromatic phosphate ester compound (D) has a structure represented by the following Formula 4:

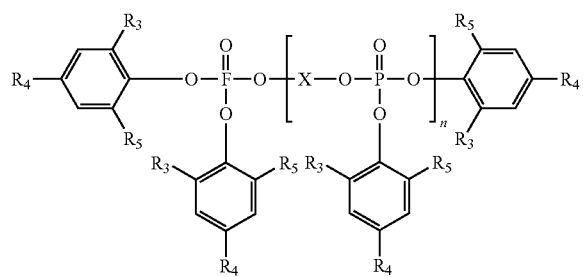

[Formula 4]

wherein $R_3$, $R_4$ and $R_5$ are each independently hydrogen or $C_1$-$C_4$ alkyl; X is $C_6$-$C_{20}$ aryl or alkyl-substituted $C_6$-$C_{20}$ aryl derivative from resorcinol, hydroquinol or bisphenol-A; and n is an integer of 0 to 4.

5. The flame retardant styrenic resin composition of claim 3, wherein said phosphate compound (E) has a structure represented by the following Formula 5:

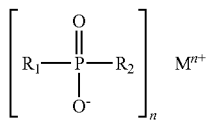

[Formula 5]

wherein $R_1$ and $R_2$ are each independently hydrogen or $C_1$-$C_4$ alkyl; M is a metal selected from the group consisting of Al, Mg, K, Zn and Ca; and n is an integer of 1 to 3.

6. The flame retardant styrenic resin composition of claim 1, further comprising less than or equal to about 30 parts by weight of an additive selected from the group consisting of heat stabilizers, anti-drip agents, anti-oxidants, compatibilizers, light stabilizers, plasticizers, pigments, dyes, inorganic additives and combinations thereof, based on about 100 parts by weight of said base resin (A)+(B).

7. The flame retardant styrenic resin composition of claim 1, wherein said symmetric cyclic phosphonate compound is represented by the following Formula I-1:

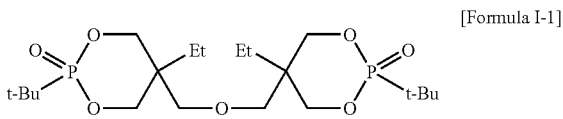

[Formula I-1]

wherein Et is ethyl and t-Bu is tert-butyl.

8. The flame retardant styrenic resin composition of claim 2, wherein the base resin comprises about 65 to about 90% by weight of the styrenic resin and about 10 to about 35% by weight of the polyphenylene ether resin, based on the total weight of the base resin comprising (A)+(B).

9. The flame retardant styrenic resin composition of claim 8, wherein the base resin comprises about 70 to about 85% by weight of the styrenic resin and about 15 to about 30% by weight of the polyphenylene ether resin, based on the total weight of the base resin comprising (A)+(B).

10. The flame retardant styrenic resin composition of claim 1, wherein the styrenic resin comprises a rubber modified aromatic vinyl resin.

11. The flame retardant styrenic resin composition of claim 1, comprising the symmetric cyclic phosphonate compound in an amount of about 1 to about 40 parts by weight, based on about 100 parts by weight of the base resin (A)+(B).

12. The flame retardant styrenic resin composition of claim 11, comprising the symmetric cyclic phosphonate compound in an amount of about 2.5 to about 35 parts by weight, based on about 100 parts by weight of the base resin (A)+(B).

13. An article formed of a composition according to claim 1.

14. The flame retardant styrenic resin composition of claim 1, wherein $R_1$ and $R_2$ are each independently $C_1$-$C_6$ alkyl.

* * * * *